(12) United States Patent
Xu et al.

(10) Patent No.: US 12,247,085 B2
(45) Date of Patent: Mar. 11, 2025

(54) HYBRIDOMA CELL LINE OF SECRETING CYPROHEPTADINE MONOCLONAL ANTIBODIES AND PREPARATION METHOD THEREOF

(71) Applicant: JIANGNAN UNIVERSITY, Wuxi (CN)

(72) Inventors: Chuanlai Xu, Wuxi (CN); Hua Kuang, Wuxi (CN); Wei Jiang, Wuxi (CN); Liguang Xu, Wuxi (CN); Wei Ma, Wuxi (CN); Liqiang Liu, Wuxi (CN); Xiaoling Wu, Wuxi (CN); Shanshan Song, Wuxi (CN); Yongming Hu, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 18/146,783

(22) Filed: Dec. 27, 2022

(65) Prior Publication Data

US 2023/0133974 A1    May 4, 2023

Related U.S. Application Data

(62) Division of application No. 16/221,873, filed on Dec. 17, 2018, now Pat. No. 11,603,414.

(30) Foreign Application Priority Data

Mar. 16, 2018 (CN) .......................... 201810219839.2

(51) Int. Cl.
| | | |
|---|---|---|
| *C07K 16/44* | (2006.01) |
| *C07K 16/06* | (2006.01) |
| *C07K 16/12* | (2006.01) |
| *C12N 5/09* | (2010.01) |
| *G01N 33/12* | (2006.01) |

(52) U.S. Cl.
CPC ............ *C07K 16/44* (2013.01); *C07K 16/065* (2013.01); *C07K 16/1289* (2013.01); *C12N 5/0693* (2013.01); *G01N 33/12* (2013.01)

(58) Field of Classification Search
None
See application file for complete search history.

(56) References Cited

FOREIGN PATENT DOCUMENTS

| CN | 104792989 B | 9/2016 |
| CN | 104109112 B | 2/2017 |
| CN | 108424880 A | 8/2018 |

OTHER PUBLICATIONS

Guo, Mengyuan, et al; Ultrasensitive immunochromatographic strip for detection of cyproheptadine; Food and Agricultural Immunology; 2018, 29: 1, 941-952.

Huang Shi-xin et al., Development and Performance Measurement of Cyproheptadine ELISA Test Ki Journal of China Veterinary drug, 2016, 50 (11 ): 44-4 (English abstract is included).

*Primary Examiner* — Brian Gangle
(74) *Attorney, Agent, or Firm* — HAUPTMAN HAM, LLP

(57) ABSTRACT

A hybridoma cell line of secreting cyproheptadine monoclonal antibodies with a preservation number of CGMCC No. 14699 belongs to the field of food safety immunological detection. BALB/c mice are immunized through one time immunization with complete freund's adjuvant, three times of booster immunization with incomplete freund's adjuvant and one time of rush immunization with cyproheptadine complete antigen without adjuvant; the spleen cells from BALB/C mice immunized with high potency and low value of IC50 are fused with murine myeloma cells; and then the hybridoma cell line is obtained through indirect competitive ELISA screening and three sub-clones. The monoclonal antibody secreted by this cell line has good specificity and detection sensitivity to cyproheptadine (value of IC50 is 0.37 ng/ml), being suitable for detection of cyproheptadine in food.

1 Claim, 2 Drawing Sheets

HYBRIDOMA CELL LINE OF SECRETING CYPROHEPTADINE MONOCLONAL ANTIBODIES AND PREPARATION METHOD THEREOF

CROSS-REFERENCE TO RELATED APPLICATIONS

This application is a Divisional of U.S. application Ser. No. 16/221,873, filed Dec. 17, 2018, which claims priority from China Application Serial Number 201810219839.2, filed on Mar. 16, 2018, the entire disclosures of which is hereby incorporated by reference herein in their entireties.

BACKGROUND OF THE INVENTION

1. Technical Field

The invention relates to the hybridoma cell line of secreting cyproheptadine monoclonal antibodies and preparation method thereof, belongs to the technical field of food safety and immunological detection.

2. Background Art

Cyproheptadine (CHP) is an antihistamine and an H1 receptor antagonist, and has the effect of anti-5-hydroxytryptamine, which can inhibit the satiety center of the hypothalamus to stimulate appetite, increase weight and promote growth. As a result, many poor manufacturers earned illegal profits by adding the drug to animal feed and water to quickly gain weight.

However, this illegal behavior can lead to drug residues in animals, which accumulate in large quantities. When people eat these animals, these drugs will accumulate in their bodies. Since cyproheptadine can cause drowsiness, dizziness, weakness, nausea, overeating, weight gain, and even allergic shock, hemolytic anemia, mental disorder, ataxia, thick bronchial secretion, tachycardia, urinary retention and other adverse reactions, it seriously endangers human health. Therefore, it is urgently need to find a highly specific and sensitive method to detect cyproheptadine residues in food.

The traditional detection methods of cyproheptadine is high performance liquid chromatography, liquid chromatography tandem mass spectrometry, enzyme linked immunosorbent assay, immune affinity chromatographic column and electrochemical sensor etc. However, these methods of pretreatment is complicated, time-consuming, and does not apply to a large number of samples of rapid detection. In order to protect the interests of consumers, it is necessary to establish an efficient and rapid detection method for cyproheptadine.

Enzyme-linked immunoassay (ELISA) is an extremely efficient, sensitive and rapid detection methods, which requires less purity and is easy to operate, being suitable for rapid detection of a large samples. However, the precondition for the detection of cyproheptadine by enzyme-linked immunosorbent assay is to obtain monoclonal antibodies with high specificity and sensitivity to cyproheptadine. Therefore, it is critical to find a method to prepare monoclonal antibodies with high specificity and sensitivity to cyproheptadine.

The inventors attempted to prepare the monoclonal antibody of cyproheptadine was prepared by hybrid tumor cells, however it was still needed further research and validation that how to prepare cyproheptadine haptens and cyproheptadine complete antigens, how to make mice immune, whether the prepared hybrid tumor cell line can secrete the monoclonal antibody of cyproheptadine and What the specificity and sensitivity of the cyproheptadine monoclonal antibody is.

SUMMARY OF THE INVENTION

The purpose of the present invention is to obtain a kind of hybridoma cell line of secreting cyproheptadine monoclonal antibodies. The monoclonal antibody secreted by this hybrid tumor cell line has good specificity and detection sensitivity to cyproheptadine (IC50 value is 0.37 ng/mL), which could be used to establish the immunological detection method of cyproheptadine, and to detect the residues of cyproheptadine in food.

The invention provides a hybrid tumor cell line that secretes the monoclonal antibody of cyproheptadine, which has been deposited with the general microbial center of China General Microbial Culture Collection Committee (No. 3 yard 1 beichen west road chaoyang district Beijing) under Accession Number CGMCC No. 14697 on Sep. 5, 2017.

The present invention provides a preparation method for a hybrid tumor cell line of secreting cyproheptadine monoclonal antibody, and contains the following steps:

Step 1: The cyproheptadine hapten and cyproheptadine complete antigen were prepared. The Cyproheptadine complete antigen were mixed with the same amount of oil, then the emulsifier was added, and the incomplete freund's adjuvant was obtained after emulsification. The complete freund's adjuvant was obtained by adding *Mycobacterium* into incomplete freund's adjuvant. The oil is paraffin oil or vegetable oil; the emulsifier is lanolin or leaf tween 80; the *Mycobacterium* includes dead seedling.

Step 2: The obtained freund's adjuvant was injected into BALB/c mice for several times for immunization subcutaneously through the back. Complete freund's adjuvant is used for the first time for immunization, while incomplete freund's adjuvant is used to booster immunization.

Step 3: The blood samples are taken from the mice after the above immune process, and the serum immune titer and immunosuppressive ability are detected by indirect ELISA to select the mice with high cyproheptadine antibody content in serum.

Step 4: The selected mice were subjected to one last booster immunization with Incomplete Freund's adjuvant, and then, the impact immunity is performed via intraperitoneal injection, using cyproheptadine complete antigen without freund's adjuvant.

Step 5: The spleen cells and myeloma cells of BALB/c mice after impact immunity are fused by the method of polyethylene glycol (PEG1500), and the fusion cells were cultured in HAT medium. The positive cell pores were detected by indirect-ELISA, and the inhibitory effect of positive cell pores was determined by indirect competitive ELISA. Subclones of positive cells with the best inhibition were performed by limited dilution method, and the hybrid tumor cell lines that could secrete the monoclonal antibody of cyproheptadine were screened out.

Step 6: The sensitivity and specificity of the antibodies that was secreted by hybrid tumor cell lines of secreting cytheptadine monoclonal antibodies was measured by ELISA.

In an embodiment of the invention, the molecular formula of cyproheptadine hapten in step 1 is as follows:

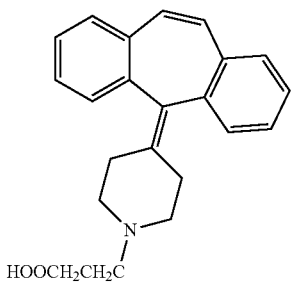

In an embodiment of the invention, the interval between the first immunization and the booster immunization in steps 2 and 4 is one month, the interval between the booster immunization is 21 days, and the interval between the booster immunization and the rush immunization is 18 days.

In an embodiment of the invention, the immune process in steps 2 and 4 comprises one time first immunization, three times booster immunization and one-time rush immunization.

In an embodiment of the invention, the blood collection in step 3 is performed on the seventh day after the end of the third immune process.

In one embodiment of the invention, the cell fusion in step 5 is performed 3 days after the end of rush immunization.

In one embodiment of the invention, the above cyproheptadine hapten is prepared by steps of:
(1) the compound 1 was dissolved in methanol solution, and ethyl chloroformate was added for stirring to obtain mixture.
(2) the cooled mixture in step (1) mentioned above was added HCL, extracted with ethyl acetate, the extracted organic layer was concentrated, and the compound 2 was obtained.
(3) the compound 2 was dissolved in ethyl alcohol and added potassium hydroxide aqueous solution to stir to get mixture.
(4) the mixture in (3) was concentrated and extracted with ethyl acetate, extracted with ethyl acetate, the extracted organic layer was concentrated, and the compound 3 was obtained.
(5) the compound 3 was dissolved in the mixture of Tetrahydrofuran THF solution containing 3-chloropropionic acid, the triethylamine was added stirring under N₂ to get mixture.
(6): the mixture in (5) was concentrated and extracted with ethyl acetate, extracted with ethyl acetate, the extracted organic layer was concentrated, and the crude product of cyproheptadine haptens was obtained.

The molecular formula of compound 1 is as follows:

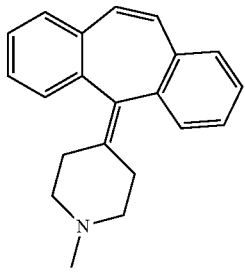 [SMILES: CN1CCC(=C2c3ccccc3C=Cc3ccccc32)CC1]

The molecular formula of compound 2 is as follows:

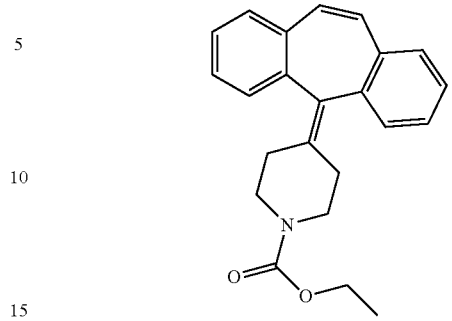

The molecular formula of the compound 3 is as follows:

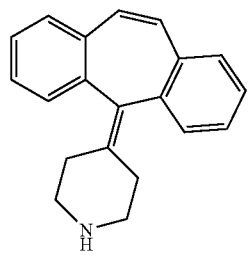 [SMILES: C1=Cc2ccccc2C(=C2CCNCC2)c2ccccc21]

In a way of implementation of the invention, in (1), 5 g compound 1 of concentration of 17.4 mmol was dissolved in 50 mL methanol solution, and 3 g ethyl chloroformate of concentration of 34.8 mmol was added for stirring under 120° C. for the night to obtain mixture.

In a way of implementation of the invention, in (2), the cooled mixture in (1) mentioned above was added HCL, extracted three times with 50 mL ethyl acetate, the extracted organic layer was dried with anhydrous $Na_2SO_4$, after vacuum concentration the 4 g compound 2 was obtained.

In a way of implementation of the invention, in (3), 4 g compound 2 of concentration of 11.6 mmol was dissolved in 64 mL ethyl alcohol and added dropwise potassium hydroxide aqueous solution of equivalent of 15 to stir under 30° C. for the night to get mixture, which the aqueous solution of potassium hydroxide is 10.3 g potassium hydroxide dissolved in 16 mL $H_2O$ to form a solution with a concentration of 174 mmol.

In a way of implementation of the invention, in (4), the mixture in step 3 was extracted three times with 50 mL ethyl after acetatevacuum concentration, and the extracted organic layer was dried with anhydrous $Na_2SO_4$, and the 2.5 g compound 3 was obtained after vacuum concentration.

In a way of implementation of the invention, in (5), 2.5 g compound 3 of the concentration of 9.2 mmol was dissolved in the mixture of 30 mL tetrahydrofuran THF solution containing 1 g 3-chloropropionic acid of the concentration of 9.2 mmol, the 1 g triethylamine of the concentration of 9.2 mmol was added stirring in 60° C. under for the night $N_2$ to get mixture.

In a way of implementation of the invention, in (6), the mixture in (5) was 30 mL extracted three times with ethyl acetate after vacuum concentration, the extracted organic layer was dried with anhydrous $Na_2SO_4$ and vacuum concentrated, and the crude product of cyproheptadine haptens was obtained.

In a way of implementation of the invention, in (6), after purification by silica gel chromatography (DCM/MeOH=20:1), 400 mg haptens were obtained.

The invention provides application of cyproheptadine hapten in the preparation cyproheptadine complete antigen, cyproheptadine antibody and a hybrid tumor cell line that secretes the monoclonal antibody of cyproheptadine monoclonal antibody.

The invention provides a preparation method for the cyproheptadine complete antigen, which the cyproheptadine haptens was taken into brown flask adding IVIES buffer solution to dissolve, EDC and NHS was added stirring to get the activated liquid; the keyhole limpet haemocyanin KLH was dissolved in CB solution, the activated liquid was added adjusting pH and reacting. The cyproheptadine complete antigen was obtained after isolating complete antigens and uncoupled small molecules.

The molecular formula of the cyproheptadine hapten is as follows:

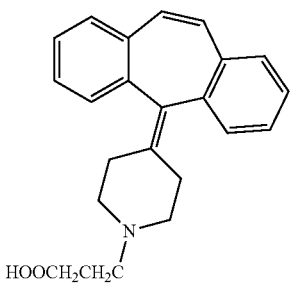

The invention provides a preparation method for the cyproheptadine complete antigen, which 5 mg cyproheptadine haptens was taken into brown flask adding 1 mL MES buffer solution of pH4.7 and the concentration of 0.1M to dissolve, 10 mg EDC and 6 mg NHS was added stirring for 6-8 h to get the activated liquid; the keyhole limpet haemocyanin KLH was dissolved in CB solution, the activated liquid was added adjusting pH to 9.0 with NaOH of the concentration of 1M, keeping in the dark and reacting for night. After isolating complete antigens and uncoupled small molecules, and identified by uv method, the cyproheptadine complete antigen was obtained.

The molecular formula of the cyproheptadine hapten is as follows:

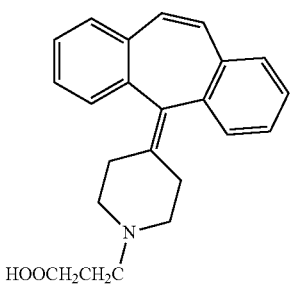

The invention provides an application of cyproheptadine complete antigen characterized by the use of the cyproheptadine complete antigen for the preparation of cyproheptadine monoclonal antibodies.

The present invention provides a monoclonal antibody of cyproheptadine, which is obtained by secretion of a hybrid tumor cell line with the preservation number CGMCC no. 14697.

The invention provides a preparation method of cyproheptadine monoclonal antibody, BALB/c mice were intraperitoneally injected with paraffin oil, and then intraperitoneally injected with hybrid tumor cells of secreting cyproheptadine monoclonal antibodies. After injection, ascites were collected and purified, then the monoclonal antibody was preserved at low temperature.

In another embodiment, BALB/c mice with 8 to 10 weeks, were intraperitoneally injected with paraffin oil 1 mL each. After 7 days, each mouse intraperitoneally is injected with 1×106 hybrid tumor cells. From 7 days start collecting ascites, purified by bitter-ammonium sulfate law, the monoclonal antibody was preserved at −20° C.

The present invention provides an application of cyproheptadine monoclonal antibody in specifically identify cyproheptadine.

The present invention provides an application of a hybrid tumor cell line secreting cyproheptadine monoclonal antibody or the cyproheptadine hapten or the cyproheptadine complete antigen in obtaining detection kit The advantages of the invention are:

The monoclonal antibody cell line obtained by the invention has a good detection sensitivity and specificity for cyproheptadine (IC50 value is 0.37 ng/ml).

The invention provides a new synthetic method of cyproheptadine hapten, complete antigen and coating antigen.

The monoclonal antibody cell line obtained by the invention can be used for immunoassay detection.

Preserve Biological Materials

A hybrid tumor cell line that secretes monoclonal antibodies to cyproheptadine, which the classification is called monoclonal cell lines, has been deposited with the general microbial center of the China General Microbial Culture Collection Committee (No. 3, yard 1, beichen west road, chaoyang district, Beijing) under Accession Number CGMCC No. 14697 on Sep. 5, 2017.

DESCRIPTION OF PREFERRED EMBODIMENTS

Figure 1:
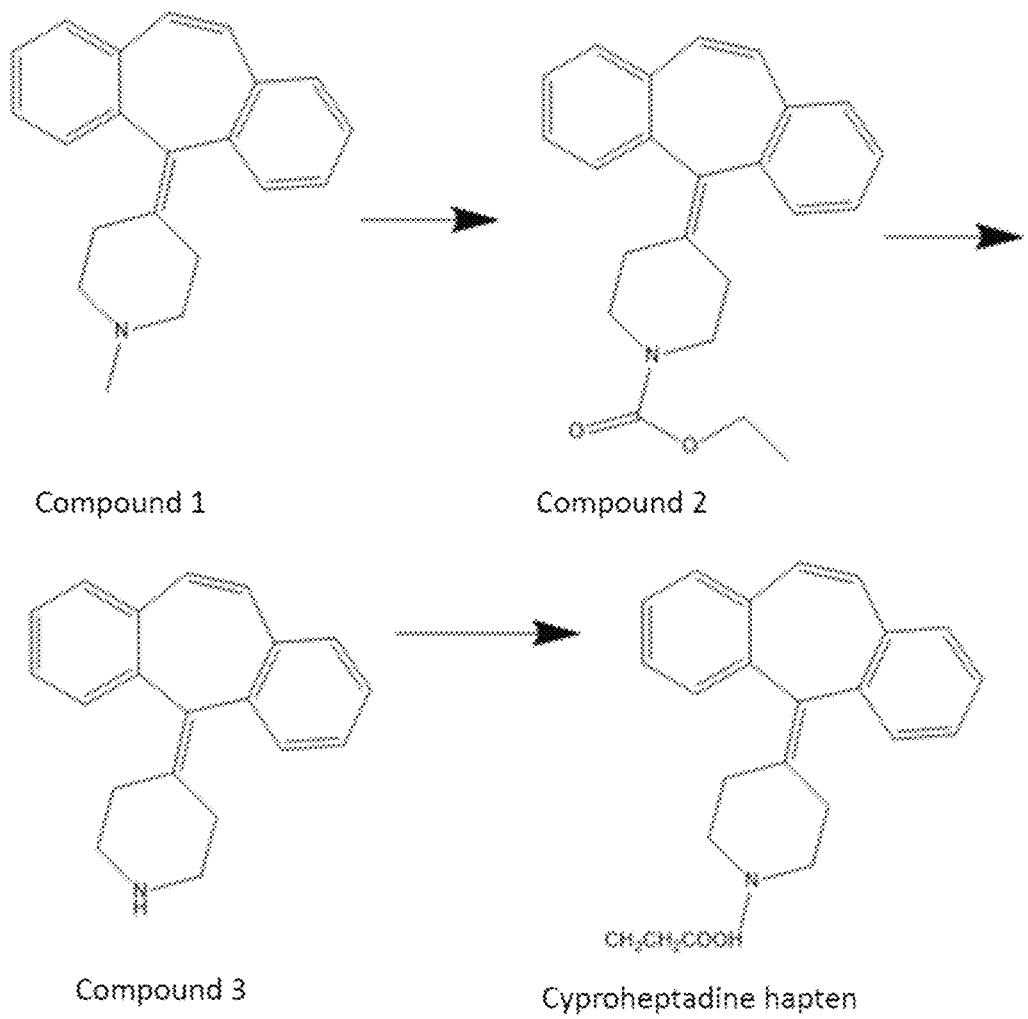
FIG. 1 shows the synthetic process of cyproheptadine haptens.

The detailed implementation of the invention is further described as follows. The following embodiments are used to illustrate the invention, but not to limit the scope of the invention.

Example 1

Synthesis of Cyproheptadine Hapten 5 g compound 1 of concentration of 17.4 mmol was dissolved in 50 mL methanol solution, and 3 g ethyl chloroformate of concentration of 34.8 mmol was added for stirring under 120° C. for the night to obtain mixture. the cooled mixture mentioned above was added HCL, extracted three times with 50 mL ethyl acetate, the extracted organic layer was dried with anhydrous Na2SO4, after vacuum concentration the 4 g compound 2 was obtained. 4 g compound 2 of concentration of 11.6 mmol was dissolved in 64 mL ethyl alcohol and added dropwise potassium hydroxide aqueous solution of equivalent of 15 to stir under 30° C. for the night to get mixture, which the aqueous solution of potassium hydroxide is 10.3 g potassium hydroxide dissolved in 16 mL H$_2$O to form a solution with a concentration of 174 mmol. the mixture was extracted three times with 50 mL ethyl after acetatevacuum concentration, and the extracted organic layer was dried with anhydrous Na$_2$SO$_4$, and the 2.5 g compound 3 was obtained after vacuum concentration. 2.5 g compound 3 of the concentration of 9.2 mmol was dissolved in the mixture of 30 mL tetrahydrofuran THF solution containing 1 g 3-chloropropionic acid of the concentration of 9.2 mmol, the 1 g triethylamine of the concentration of 9.2 mmol was added stirring in 60° C. under for the night N$_2$ to get mixture. the mixture was 30 mL extracted three times with ethyl acetate after vacuum concentration, the extracted organic layer was dried with anhydrous Na$_2$SO$_4$ and vacuum concentrated, and the crude product of cyproheptadine haptens was obtained. After purification by silica gel chromatography (DCM/MeOH=20:1), 400 mg haptens were obtained.

Example 2

Figure 2:
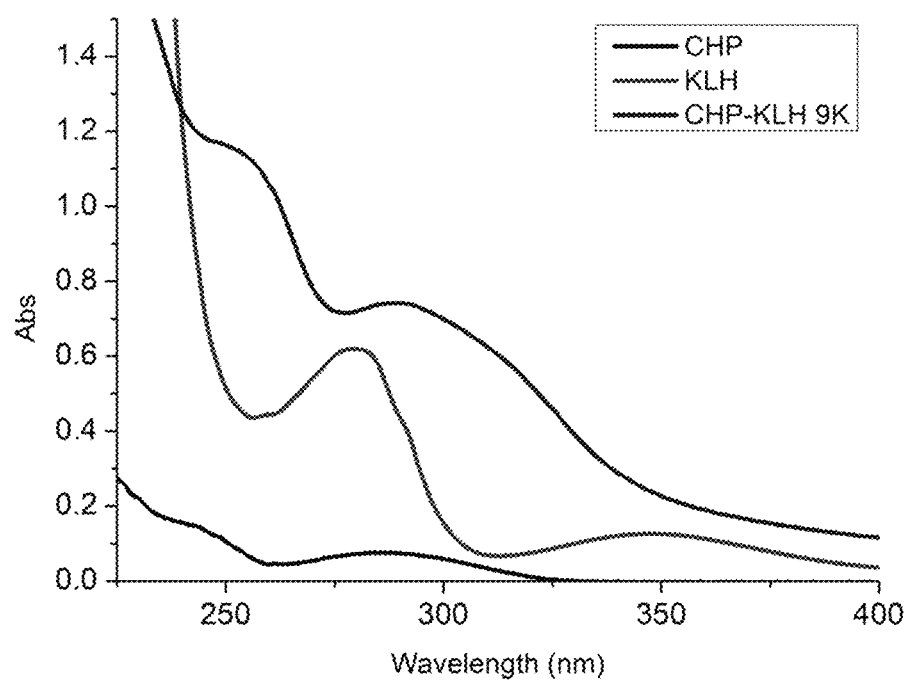
FIG. 2 shows the UV characterization of cyproheptadine complete antigen
Figure 3:
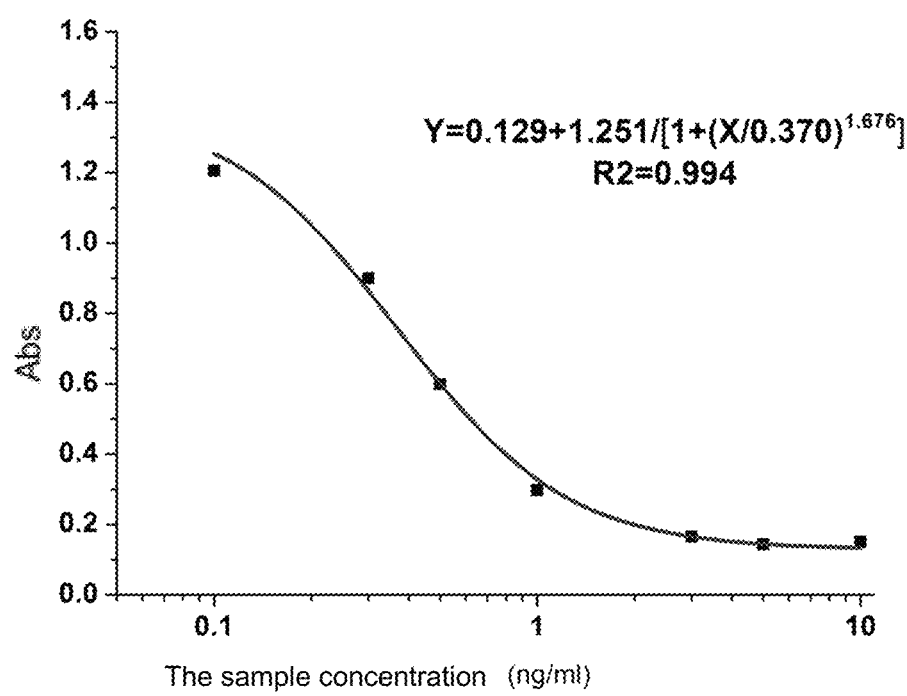
FIG. 3 shows the standard curve of inhibition of cyproheptadine by cyproheptadine monoclonal antibody.

Synthesis of Cyproheptadine Complete Antigen 5 mg cyproheptadine haptens was taken into brown flask adding 1 mL MES buffer solution of pH4.7 and the concentration of 0.1M to dissolve, 10 mg EDC and 6 mg NHS was added stirring for 6-8 h to get the activated liquid; the keyhole limpet haemocyanin KLH was dissolved in CB solution, the activated liquid was added adjusting pH to 9.0 with NaOH of the concentration of 1M, keeping in the dark and reacting for night. After isolating complete antigens and uncoupled small molecules, and identified by uv method, the cyproheptadine complete antigen was obtained (the uv characterization effect of cyheptadine complete antigen of the present invention is shown in FIG. 2).

Example 3

Preparation of Hybrid Tumor Cell Lines that Secrete the Monoclonal Antibody of Cyproheptadine
Animal Immunization After the cyproheptadine complete antigen and equivalent freund's adjuvant were mixed and emulsified, BALB/c mice were immunized by subcutaneous injection in the neck and back. For the first immunization, complete freund's adjuvant was used. For two times booster immunization, incomplete freund's adjuvant was used. The blood collection is performed on the seventh day after the end of the third immune process. Blood samples were taken from the mice after the above immune process, and the serum immune titer and immunosuppressive ability were detected by indirect ELISA to select the mice with high cyproheptadine antibody content in serum. The selected mice were subjected to 4th booster immunization with incomplete freund's adjuvant, and then, the rush immunization is performed via intraperitoneal injection, using cyproheptadine complete antigen without freund's adjuvant. (the interval between the booster immunization is 21 days, and the interval between the booster immunization and the rush immunization is 18 days).

2. Cell Fusion

After 3 days of shock immunity, cell fusion was performed by PEG (polyethylene glycol, with a molecular weight of 1500). The steps were as follows:

The spleen of the mouse was taken aseptically, spleen cell suspension was obtained by grinding and screening with 200 mesh cells and then Counting cells Sp2/0 cells was collected, and suspended in rpm-1640 basic medium for cell counting.

Spleen cells and sp2/0 cells were mixed in a ratio of 1:10, centrifuged and fused with 50% PEG for 1 mi, the basic culture medium RPMI-1640 was added from slow to fast, after the centrifugal cells suspended in RPMI-1640 filter medium containing 20% fetal bovine serum and 2% of the 50×HAT, and added to the 96 cell culture plate at 37° C. and cultivating in 5% CO2 incubator.

Cell Screening and Cell Line Establishment

On the third day of cell fusion, the fusion cells were partially replaced with the rpm-1640 screening medium, and on the fifth day, the cells were fully replaced with the rpm-1640 transition medium containing 20% fetal bovine serum and 1% 100×HT, and the supernatant was taken on the seventh day for screening.

Screening is divided into two steps: the first step was to screen out the positive cells by indirect ELISA; in the second step, Melo was selected as the standard product, and the inhibitory effect of positive cells was measured by indirect competitive ELISA. Cell pores that had good inhibition on all cyproheptadine standard products were selected, and subclone was conducted by finite dilution method. The same method was used for detection, and the cell lines were obtained after repeated for three times.

4. Cell Lines are Frozen

The hybrid tumor cell line named monoclonal cell line has been deposited with the general microbial center of China General Microbial Culture Collection Committee (No. 3 yard 1 beichen west road chaoyang district Beijing) under Accession Number CGMCC No. 14697 on Sep. 5, 2017.

Example 4 Preparation and Identification of Cyproheptadine Monoclonal Antibody

BALB/c mice with 8 to 10 weeks, were intraperitoneally injected with paraffin oil 1 mL each. After 7 days, each mouse intraperitoneally is injected with 1×106 hybrid tumor cells secreting cyproheptadine monoclonal antibody. From 7 days start collecting ascites, the monoclonal antibody was obtained after purification and preserved at −20° C.

Using indirect competition ELISA, the IC50 value of the cyproheptadine monoclonal antibody was measured to be 0.37 ng/mL and the crossover value of the cyproheptadine analogue was measured to be less than 10%, which indicated that it has good sensitivity to cyproheptadine and could be used for cyproheptadine immunoassay.

Example 5

Application of Cyproheptadine Monoclonal Antibody

Monoclonal antibodies prepared by hybrid tumor cell lines were applied to the addition and recovery test of ELISA about cyproheptadine. The specific steps are as follows:

The Solution Configuration

Carbonate buffer solution (CBS): Weigh Na$_2$CO$_3$ 1.59 g and NaHCO$_3$1.59 g, then mix with steaming water, plus double steamed water to 800 mL, adjust pH value to 9.6, add double steaming water for constant volume (1000 mL), store at 4° C.;

Phosphate Buffer solution (PBS): 8.00 g NaCl, 0.2 g KCl, 0.2 g KH$_2$PO$_4$, 2.9 g Na$_2$HPO$_4$·12 H$_2$O, dissolved in 800 mL pure water, pH was adjusted to 7.2~7.4 with NaOH or HCl, then the capacity was constant to 1000 mL;

PBST: Add 0.5 ml Tween-20 to 1000 mL PBS solution (0.01 mol/L, pH 7.4);

Antibody Diluent: Washing buffer containing 0.1% gelatin;

TMB Substrate: Mixture of solution A and solution B with 1:5; Solution A: $Na_2HPO_4 \cdot 12H_2O$ 18.43 g, citric acid 9.33 g, constant to 1000 mL with pure water. Solution B: 60 mg TMB dissolved in 100 mL ethylene glycol.

(2) Coating: coating antigen CLA-CMO-OVA had reacted for 2 h after serial dilution of the carbonate buffer (pH 9.6, 0.05 m) from 1 µg/mL, 100 µL/hole at 37° C.

(3) Washing: the solution in the plate was poured out and wash it 3 times with wash solution, 3 min each.

(4) Sealing: After pat dry, 200 µL/hole sealing fluid was added to reaction within 2 h at 37° C., drying after washing.

(5) Sample adding: antiserum was diluted from the ratio of 1:1000, and was added into the degree of the dilution of coating hole, 100 µL/hole, and had reacted at 70° C. for 30 min. After fully washing, HRP-Goat anti Mouse IgG that had diluted with the ratio of 1:3000 was added and reacted at 37° C. for 30 min, 100 µL/hole;

(6) Coloration: The enzyme label plate was taken out, after washing, each hole was added into TMB Color liquid, and reacted at 37° C. for 15 min avoiding light.

(7) Termination and determination: To terminate the reaction, 50 µL termination solution was added to each hole, and then the value of $OD_{450}$ of each hole was measured with an enzyme marker.

(8) Reading result: The ELISA titer of serum was the highest dilution factor corresponding to the serum with the $OD_{450}$ value greater than or equal to 2.1 times of the negative control hole (i.e., P/N≥2.1).

The IC50 of the monoclonal antibody was 0.37 ng/mL, indicating a good sensitivity to cyproheptadine and can be used for cyproheptadine immunoassay.

Serum test results of mice after three immunizations:

| The concentration of standard | The dilution ratio of | The concentration of coating antigen | | |
|---|---|---|---|---|
| ng/ml | mice serum | 1 µg/ml | 0.3 µg/ml | 0.1 µg/ml |
| 0 ng/ml | 1k | 2.983 | 2.623 | 1.278 |
|  | 3k | 2.618 | 2.134 | 0.844 |
|  | 9k | 1.973 | 1.328 | 1.497 |
| 20 ng/ml | 1k | 2.163 | 1.28 | 0.419 |
|  | 3k | 1.597 | 0.751 | 0.248 |
|  | 9k | 0.746 | 0.338 | 0.136 |

| Small molecule to be measured | Cell screening process | Cell line number | OD (without standard) | OD (Standard addition concentration X ng/ml) |
|---|---|---|---|---|
| cyproheptadine | After the fusion | 4A11 | 1.768 | 0.282(5 ng/ml) |
|  | 1 g | 2H12 | 1.338 | 0.078(2 ng/ml) |
|  | 2 g | 4B1 | 1.244 | 0.468(0.5 ng/ml) |
|  | 3 g | 3E' 10 | 1.379 | 0.612(0.5 ng/ml) |

Contrast Example 1: Preparation of Hybrid Tumor Cell Lines Secreting Cyproheptadine Monoclonal Antibody Replacing the coating antige in the above embodiments with BSA, it was found that cyproheptadine conjugated OVA was more effective as the coating antigen.

| The coating antigen | The concentration of coating | The concentration of antibody | ODmax | IC50(ng/ml) |
|---|---|---|---|---|
| CHP-OVA 40:1 | 0.3 µg/ml | 0.3 µg/ml | 1.457 | 0.37 |
| CHP-BSA 60:1 | 0.3 µg/ml | 0.3 µg/ml | 1.895 | 0.514 |

Contrast Example 2: Preparation of Hybrid Tumor Cell Lines Secreting Cyproheptadine Monoclonal Antibody In the above embodiment, the number of addition and exemption was changed to the serum test results of mice after the Secondary immunization and exemption:

| The concentration of standard | The dilution ratio of | The concentration of coating antigen | | |
|---|---|---|---|---|
| ng/ml | mice serum | 1 µg/ml | 0.3 µg/ml | 0.1 µg/ml |
| 0 ng/ml | 1k | 2.683 | 2.323 | 0.978 |
|  | 3k | 2.318 | 1.834 | 0.544 |
|  | 9k | 1.673 | 1.028 | 0.297 |
| 20 ng/ml | 1k | 2.141 | 1.318 | 0.519 |
|  | 3k | 1.647 | 0.815 | 0.359 |
|  | 9k | 0.864 | 0.479 | 0.018 |

Compared with the three times booster immunizations, the titer and inhibition of serum after the two times booster immunizations were not as good as those after the three times booster immunizations.

The above description is only a preferred method of implementation of the invention and is not used to limit the invention. It should be noted that, for ordinary technical personnel in the field of technology, some improvements and variations can be made under the technical principles of the invention. These improvements and variations should also be considered as the scope of protection of the invention.

What is claimed is:

1. A method for preparing a hybrid tumor cell line that secretes cyproheptadine monoclonal antibodies with Deposit Number CGMCC No. 14697, comprising:
synthesis of cyproheptadine hapten, synthesis of cyproheptadine complete antigen, animal immunization, cell fusion, cell screening and cell line establishment, the hybrid tumor cell line was obtained, and named monoclonal cell line with the Deposit Number CGMCC No. 14697;
wherein the cyproheptadine hapten is as follows:

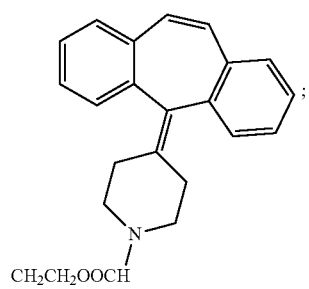

the synthesis of cyproheptadine hapten comprises:
① the compound 1 is dissolved in methanol solution, and ethyl chloroformate is added for stirring to obtain mixture 1, wherein the molecular formula of compound 1 is as follows:

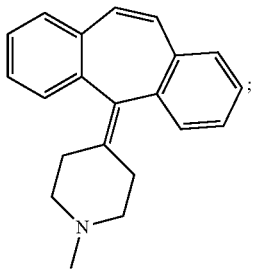 [SMILES: CN1CCC(=C2c3ccccc3C=Cc3ccccc32)CC1]

② the mixture 1 in ① mentioned above is cooled, and hydrochloride (HCl) is added in to obtain mixture 2, and then extracted with ethyl acetate, the extracted organic layer is concentrated, and the compound 2 is obtained;
③ an aqueous solution of potassium hydroxide is added drop by drop to the ethanol mixture of the compound 2 and stirred to get mixture 3, wherein the molecular formula of compound 2 is as follows:

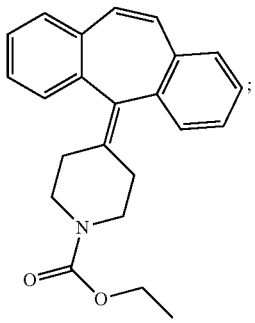 [SMILES: CCOC(=O)N1CCC(=C2c3ccccc3C=Cc3ccccc32)CC1]

④ the mixture 3 in ③ is concentrated and extracted with ethyl acetate, and the extracted organic layer is dried, and the compound 3 is obtained, wherein the molecular formula of the compound 3 is as follows:

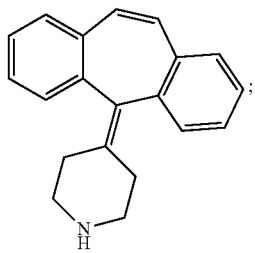 [SMILES: C1=Cc2ccccc2C(=C2CCNCC2)c2ccccc21]

⑤ the compound 3 is dissolved in tetrahydrofuran (THF) solution containing 3-chloropropionic acid, add triethylamine and stir under $N_2$ to get mixture 4;
⑥ the mixture 4 in ⑤ is concentrated and extracted with ethyl acetate, and the extracted organic layer is dried, and the crude product of cyproheptadine hapten is obtained, after purification by silica gel chromatography (DCM/MeOH=20:1), cyproheptadine hapten was obtained.

* * * * *